(12) United States Patent
Bara

(10) Patent No.: US 6,224,851 B1
(45) Date of Patent: *May 1, 2001

(54) USE OF A VOLATILE POLYFLUORINATED SOLVENT AS AN ANTITRANSFER AGENT IN COSMETIC PRODUCTS

(75) Inventor: Isabelle Bara, Paris (FR)

(73) Assignee: L'Oreal, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/220,777

(22) Filed: Dec. 28, 1998

(30) Foreign Application Priority Data

Dec. 29, 1997 (FR) .................................................. 97 16628
Jun. 30, 1998 (FR) .................................................. 98 08338

(51) Int. Cl.[7] ............................ A61K 7/42; A61K 7/021; A61K 7/025; A61K 7/035; A61K 7/06
(52) U.S. Cl. ................................ 424/59; 424/63; 424/64; 424/69; 424/70.7; 424/401; 514/747; 514/759; 514/845; 514/938
(58) Field of Search .................... 424/59, 61, 63, 424/69, 40; 514/747, 759, 845, 938

(56) References Cited

U.S. PATENT DOCUMENTS 5,741,499 * 4/1998 Arnould et al. .

5,851,539 * 12/1998 Mellul et al. ........................ 424/401

FOREIGN PATENT DOCUMENTS 0 595 683 A1   5/1994   (EP) .
2 593 392      7/1987   (FR) .
2 756 176      5/1998   (FR) .

OTHER PUBLICATIONS

Databse JPO on West, Abstract of JP 05221829 A (Ofuku, Hiromi and Takano, Toru) 1993.*

Chemical Abstracts 117:137 461 & JP 04 139 121 A, May 13, 1992.

Chemical Abstracts 110:160 222 & JP 63 002 916 A, Jan. 7, 1988.

* cited by examiner

Primary Examiner—Diana Dudash
Assistant Examiner—Alysia Berman
(74) Attorney, Agent, or Firm—Nixon & Vanderhye P.C.

(57) ABSTRACT

The present invention provides a process for making transfer resistant make-up or sun-screen cosmetic compositions containing particles, which process includes introducing at least one volatile polyorganohalogen solvent, the halogen atom being fluorine, as an anti-transfer agent.

5 Claims, No Drawings

USE OF A VOLATILE POLYFLUORINATED SOLVENT AS AN ANTITRANSFER AGENT IN COSMETIC PRODUCTS

The present invention relates to the use of a certain class of volatile polyorganohalogen compounds, in which the halogen atom is a fluorine, in antisun or make-up or sun-screen cosmetic compositions in order to avoid so-called transfer phenomena.

In cosmetic compositions of this type, the term transfer means the displacement of a fraction of the composition by contact with another support, whether of the same nature or of different nature. Thus, when they are intended for make-up, such as eyeshadows, eyeliners or mascaras, they can be transferred onto the hands by rubbing or by contact of the hands with the eyes. When these compositions are lipsticks, they can be transferred onto the teeth, the hands or onto the cheeks of another person.

Irrespective of the type of composition they are, they can also, by transfer, stain napkins and leave imprints on glasses, cups and other containers.

In addition, when the compositions are foundations, the foundation can also transfer onto shirt collars and thus stain them.

In addition to this transfer problem, make-up compositions can also exhibit migration phenomena, i.e. the compositions have a tendency to travel inside the wrinkles and/or fine lines on the skin, in particular in the case of foundations, in the fine lines around the lips in the case of lipsticks, and in the folds of the eyelids in the case of eyeshadows.

These transfer and migration phenomena are particularly detrimental since they give rise to an aesthetically unappealing effect and to a certain number of drawbacks as mentioned above.

In order to overcome this, it has already been proposed, in particular in U.S. Pat. No. 5,505,937, to use volatile oils, in particular cyclic silicones, as well as hydrocarbon-based products such as $C_8$–$C_{20}$-iso-paraffins combined with a silicone resin and with waxes.

Although this type of make-up composition makes it possible to avoid the transfer phenomena, there is nevertheless formation of a dry film on the skin, this film consisting of waxes and pigments with a matt appearance, which is associated with a surface state of the heterogeneous film.

It has also been proposed to make transfer-resistant make-up products, by using aqueous dispersions of hydrophobic polymers or latices, which, after drying on the skin, give a dry film which can have a certain level of sheen.

Nevertheless, the drawback of these aqueous dispersions of hydrophobic polymers is associated with a level of discomfort and a difficulty in applying them to the skin, in particular to the lips in the case of lipsticks.

After many studies on various types of compounds, it has been observed, surprisingly and unexpectedly, that by using a certain class of volatile polyorganohalogen solvents in which the halogen atom is fluorine, it is possible to overcome, in a particularly satisfactory and effective manner, the drawbacks arising due to the transfer and migration problems.

Another particularly appreciable advantage is to be able to obtain the compositions in total safety, since these solvents, referred to hereinbelow as volatile polyfluorinated solvents, have no flash point, which allows the compositions to be prepared at high temperature, and thus has a certain advantage when substances with a melting point above room temperature are used.

Lastly, the use of volatile polyfluorinated solvents makes it easier to incorporate high concentrations of non-volatile fluorinated derivatives into the compositions, these derivatives being entirely miscible with the volatile polyfluorinated solvents. A highly fluorinated, shiny or satin residual film which is water-resistant and fat-resistant can thus be obtained.

The subject of the present invention is thus the use, in a make-up or sun-screen cosmetic composition containing particles of pigment and/or of filler, of at least one volatile polyorganohalogen solvent, as anti-transfer agent, the halogen atom being fluorine and the said solvent having a vapour pressure of greater than 20 mba (2000 Pa) at 25° C. and preferably greater than 40 mba (4000 Pa).

Among the volatile polyfluorinated solvents which can be used according to the invention and which satisfy the vapour pressure criterion mentioned above, mention may be made in particular of:

1) the perfluorocycloalkyl compounds corresponding to the formula (I) below:

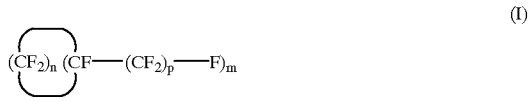

in which:
n is 3, 4 or 5,
m is 1 or 2, and
p is 1, 2 or 3
with the proviso that when m=2, the groups are not necessarily alpha to each other, 2) the fluoroalkyl or heterofluoroalkyl compounds corresponding to formula (II) below:

in which:
t is 0 or 1,
n is 0, 1, 2 or 3
X is a linear or branched divalent perfluoroalkyl radical containing from 2 to 5 carbon atoms, and
Z represents O, S or NR, R being hydrogen, a radical —$(CH_2)_n$-$CH_3$ or —$(CF_2)_m$—$CF_3$, m being 2, 3, 4 or 5, 3) the perfluoroalkane compounds corresponding to formula (III) below:

in which:
n is 2 to 6, and 4) the perfluoromorpholine derivatives corresponding to formula (IV) below:

in which:
R represents a $C_1$–$C_4$ perfluoroalkyl radical.

Among the perfluorocycloalkyl compounds of formula (I), mention may be made in particular of perfluoromethylcyclopentane and perfluorodimethylcyclohexane, which are respectively sold under the names Flutec PC1® and Flutec PC3® by the company BNFL Fluorochemicals Ltd., and perfluorodimethylcyclobutane.

Among the fluoroalkyl or heterofluoroalkyl compounds of formula (II) mention may be made in particular of methoxynonafluorobutane, sold under the name HFE7100 by the Company 3M, and ethoxynonafluorobutane sold under the name HFE-7200® by the company 3M.

Among the perfluoroalkane compounds of formula (III), mention may be made in particular of dodecafluoropentane and tetradecafluorohexane.

Among the perfluoromorpholine derivatives of formula (IV), mention may be made in particular of 4-trifluoromethylperfluoromorpholine and 4-pentafluoroethylperfluoromorpholine.

The volatile polyfluorinated solvents as defined above must also satisfy the criterion of the boiling point, which needs to be between 20 and 75° C. and preferably between 25 and 65° C.

In the make-up or sun-screen compositions, the proportion of volatile polyfluorinated solvent is generally between 2 and 98% by weight, but preferably between 5 and 70% by weight, relative to the total weight of the composition.

The pigments in the make-up or sun-screen compositions and the fillers are in the form of very fine particles with an average particle size of between about 0.02 and about 50 µm.

The pigments in the compositions can be inorganic or organic or alternatively in the form of metal lakes. Among these pigments, mention may be made of titanium dioxide, zinc oxide, D&C Red No. 36 and D&C Orange No. 17, the D&C Red Nos. 7, 11, 31 and 34 calcium lakes, the D&C Red No. 12 barium lake, the D&C Red No. 13 strontium lake, the FD&C Yellow No. 5, FD&C Yellow No. 6, D&C Red No. 27, D&C Red No. 21 and FD&C Blue No. 1 aluminum lakes, iron oxides, manganese violet, chromium oxide and ultramarine blue.

The fillers can be of natural or synthetic origin. Among these, mention may be made in particular of:

a) inorganic powders such as talc, kaolin, mica, silica, silicates, alumina, zeolites, hydroxyapatite, sericite, titanium micas, barium sulphate, bismuth oxychloride, boron nitride and metal powders such as aluminium powder;

b) plant powders such as cereal starch powder, corn powder, potato starch powder or rice powder;

c) organic powders such as nylon powder, polyamide powder, polyester powder, polytetrafluoroethylene powder or polyethylene powder.

These various powders can also be coated, for example, with metal salts of fatty acids, amino acids, lecithin, collagen, silicone compounds or fluoro compounds, or with any other common coating agent.

In addition to the pigments as defined above, the compositions also contain at least one dye, and, among these, mention may be made of eosin derivatives such as D&C Red No. 21 and halogenated fluoroscein derivatives such as D&C Red No. 27, D&C Orange No. 5 in combination with D& C Red No. 21 and D&C Orange No. 10.

In the make-up or sun-screen compositions, the proportion of at least one pigment and/or dye is generally between about 0.1 and about 15% by weight relative to the total weight of the composition.

The fillers can generally be present in the make-up or sun-screen products in a maximum proportion of about 98% by weight relative to the total weight of the composition.

According to a first specific embodiment of the make-up or sun-screen compositions, they are anhydrous and comprise a fatty phase in a proportion of between about 0.3 and about 90% by weight relative to the total weight of the composition.

The fatty phase generally consists of one or more fatty substances which can be chosen from oils, waxes, gum and/or fatty substances referred to as being pasty.

A—The oils in the fatty phase can be of mineral, animal, plant or synthetic origin, it being possible for them to be volatile or non-volatile at room temperature.

As oil of mineral origin, mention may be made in particular of liquid paraffin and liquid petroleum jelly.

As oil of animal origin, mention may be made in particular of squalane and perhydrosqualene.

As oil of plant origin, mention maybe made in particular of sweet almond oil, beauty-leaf oil, palm oil, avocado oil, jojoba oil, sesame oil, olive oil, castor oil and cereal germ oils such as, for example, wheatgerm oil.

As synthetic oil, mention may be made in particular of:

(1) the esters of formula (III) below:

$$R_1\text{—COOR}_2 \tag{III}$$

in which:

$R_1$ represents the residue of a higher fatty acid containing from 7 to 20 carbon atoms, and $R_2$ represents a hydrocarbon-based radical containing from 3 to 30 carbon atoms.

Among these esters, mention may be made in particular of:

purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate, esters derived from lanolic acid, such as isopropyl lanolate and isocetyl lanolate.

As other synthetic oils, mention may also be made of isododecane, isohexadecane, polyisobutenes and hydrogenated polyisobutene, as well as acetyl-glycerides, octanoates and decanoates of polyalcohols such as those of glycol and of glycerol, ricinoleates of alcohols and of polyalcohols, such as cetyl ricinoleate, propylene glycol dicaprylate and diisopropyl adipate;

(2) fatty alcohols such as oleyl alcohol, linoleyl alcohol, linolenyl alcohol, isostearyl alcohol and octyldodecanol;

(3) silicone oils such as optionally functionalized linear polydiorganosiloxanes, cyclic polydiorganosiloxanes and in particular cyclotetra- and cyclopentadimethicones and organopolysiloxanes such as alkyl, alkoxy or phenyl dimethicones and in particular phenyltrimethicone;

(4) non-volatile fluoro oils such as perfluorodecaline, perfluorophenanthrene, perfluoroalkanes and perfluoropolyethers and partially fluorinated hydrocarbon-based oils.

According to a particularly preferred form of the invention, non-volatile perfluoropolyethers are used in which correspond to formulae (IV) and (V) below:

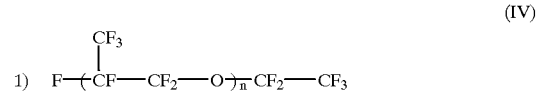

$$1) \quad F\text{—}(\text{CF}(\text{CF}_3)\text{—CF}_2\text{—O})_n\text{—CF}_2\text{—CF}_3 \tag{IV}$$

in which:

n=7 to 30,

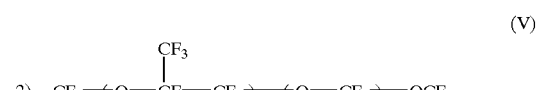

$$2) \quad \text{CF}_3\text{—}(\text{O—CF}(\text{CF}_3)\text{—CF}_2)_n\text{—}(\text{O—CF}_2)_m\text{—OCF}_3 \tag{V}$$

in which:

n and m=20 to 40.

Among these, mention may be made of those sold under the names Fomblin C® and Galden® by the company Aussimont, or alternatively under the name Fluortress LM 36® by the company Du Pont.

B—The waxes in the fatty phase can be of mineral, fossil, animal, plant or synthetic origin or alternatively can be hydrogenated oils or fatty esters which are solid at 25° C.

Among the mineral waxes, mention may be made in particular of microcrystalline waxes, paraffin, petroleum jelly and ceresine.

Among the fossil waxes, mention may be made of ozokerite and montan wax.

Among the waxes of animal origin, mention may be made of beeswax, spermaceti, lanolin wax and lanolin derivatives such as lanolin alcohols, hydrogenated lanolin, hydroxylated lanolin, acetylated lanolin, lanolin fatty acids and acetylated lanolin alcohol.

Among the waxes of plant origin, mention may be made in particular of candelilla wax, carnauba wax, Japan wax and cocoa butter.

Among the synthetic waxes, mention may be made in particular of ethylene homopolymers and copolymers of ethylene and of a monomer corresponding to formula (VI) below:

$$CH_2=CH-R_3 \quad (VI)$$

in which:

$R_3$ represents an alkyl radical containing from 1 to 30 carbon atoms or an aryl or aralkyl radical.

The alkyl radical containing from 1 to 30 carbon atoms is preferably a methyl, ethyl, propyl, isopropyl, butyl, decyl, dodecyl or octadecyl radical.

The waxes obtained by Fischer-Tropsch synthesis and silicone waxes can also be used.

Among the hydrogenated oils which are solid at 25° C. mention may be made of hydrogenated castor oil, hydrogenated palm oil, hydrogenated tallow and hydrogenated coconut oil.

Among the fatty esters which are solid at 25° C., mention may be made in particular of propylene glycol monomyristate and myristyl myristate.

As waxes which can be used in the compositions according to the invention, mention may also be made of cetyl alcohol, stearyl alcohol, mono-, di- and triglycerides which are solid at 25° C., stearic monoethanolamide, colophony and its derivatives such as glycol and glyceryl abietates, sucroglycerides and calcium, magnesium, zinc and aluminium oleates, myristates, lanolates, stearates and dihydroxystearates, and fluoro waxes.

C—The fatty substances of pasty type can be of mineral, animal, plant or synthetic origin.

Among the pasty fatty substances, mention may be made in particular of synthetic esters such as arachidyl propionate, polyvinyl laurate, polyethylene waxes and organopolysiloxanes such as alkyldimethicones, alkoxydimethicones or dimethicone esters.

Needles to say, the anhydrous compositions as defined above can also contain one or more conventional cosmetic or dermatological additives or adjuvants.

These anhydrous compositions can be in various forms such as, for example, in the form of an oily gel, a solid produce such as a compacted or cast powder, or alternatively a stick such as, for example, a lipstick.

When the compositions are in the form of an oily gel, they generally contain, besides the constituents defined above, an oily gelling agent.

Among the oily gelling agents, mention may be made in particular of metal esters such as polyoxyaluminium stearate and aluminium or magnesium hydroxystearate, fatty acid esters of glycol, triglycerides, fatty alcohol mixtures, cholesterol derivatives and in particular hydroxycholesterol, and clay minerals which swell in the presence of oil, and in particular those belonging to the montmorillonite group.

The oily gelling agents can be present in a very variable proportion depending on the desired texture of the compositions. However, in most cases, they are present in a proportion of between about 0.1 and about 30% by weight relative to the total weight of the composition.

These anhydrous compositions can be, in particular, foundations, mascaras, eyeliners, lipsticks, eyeshadows or blushers.

According to a second embodiment of the compositions according to the invention, they are dispersions, in the form of a stable water-in-oil (W/O) or oil-in-water (O/W) emulsion, these dispersions consisting essentially of (i) a fatty phase in a proportion of between about 0.1 and about 50% by weight relative to the total weight of the composition, it being possible for the said fatty phase to contain at least one fatty substance as defined above in a proportion of between about 0.1 and about 95% by weight relative to the total weight of the composition, (ii) an aqueous phase in a proportion of between about 4 and about 97% by weight relative to the total weight of the composition, and (iii) at least one emulsifier in a proportion of between about 1 and about 10% by weight relative to the total weight of the composition in emulsion form.

As emulsifier or surfactant which can be used in the compositions in the form of a W/O or O/W emulsion, mention may be made in particular of silicone surfactants and in particular those belonging to the alkyl- or alkoxy-dimethicone copolyol family. Among the alkyl- or alkoxy-dimethicone copolyols, mention may be made in particular of the compounds corresponding to the following general formula:

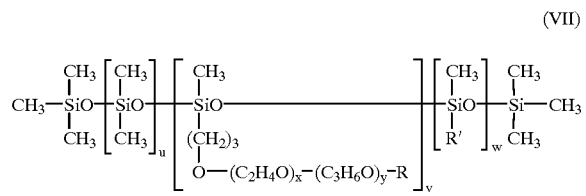

(VII)

in which:

R is a hydrogen atom, a $C_1$–$C_{16}$ alkyl or an alkoxy or acyl,

R' is a $C_8$–$C_{22}$ alkyl or alkoxy radical, u=0 to 200, v=1 to 40, w=1 to 100, the molecular weight of the radical —O—$(C_2H_4O)_x$—$(C_3H_6O)_y$—R being from 250 to 2000, x and y being chosen such that the weight ratio of the oxyethylene/oxypropylene groups is between 100:0 and 20:80.

Among the commercial products which can contain all or some of the alkyldimethicone copolyols, mention may be made in particular of those sold under the names Abil WE09®, Abil EM90® or Q2 3225C® by the company Dow Corning and 218 1138® by the company General Electric.

The surfactants can also be chosen from anionic and nonionic surfactants. In this respect, reference may be made to the document Encyclopedia of Chemical Technology, Kirk-Othmer, volume 22, pages 333–342, 3rd edition, 1979, Wiley, for the definition of the properties and functions (emulsifying) of the surfactants, in particular pages 347–377 of that reference, for the anionic and nonionic surfactants.

The surfactants of these two groups which are preferably used in the compositions according to the invention are:

among the nonionic surfactants: fatty acids, fatty alcohols, polyethoxylated or polyglycerolated fatty alcohols, such as polyethoxylated stearyl or cetylstearyl alcohol, fatty acid esters of sucrose, glucose alkyl esters, in particular polyoxyethylenated fatty esters of ($C_1$–$C_6$) alkylglucose, and among the anionic surfactants: amine stearates.

These emulsions an preferably be in the form of creams and can be used as make-up or sun-screen products. In the latter case, they contain UVA and/or UVB sunscreens and white pigments, in a variable proportion depending on the desired degree of protection.

The compositions as described above, whether of the anhydrous type or in the form of a dispersion, have excellent cosmetic properties such as, in particular, an excellent ease of application, great softness and lead to the production of a uniform make-up.

The compositions as have just been described above can also contain one or more conventional cosmetic adjuvants such as vitamins, hormones, antioxidants, preserving agents, fragrances, thickeners, moisturizers, wetting agents, anionic, nonionic or amphoteric polymers, or cosmetic or dermatological active agents.

The subject of the present invention is also the process for preparing make-up or sun-screen cosmetic composition in order to limit or suppress the so-called transfer phenomena, this process consisting in introducing into the said composition an effective amount of at least one volatile polyfluorinated solvent as defined above, which has a vapour pressure of greater than 20 mba (2000 Pa) at 25° C.

The invention will now be illustrated by the various examples which follow, in which the amounts are expressed by weight.

EXAMPLES

Example 1

Transfer-resistant lipstick

| | |
|---|---|
| - Methoxynonafluorobutane (HFE-7100) | 10 g |
| - Perfluorodecalin | 35 g |
| - Wax | 40 g |
| - Polyperfluoroisopropyl ether (Fluortress LM 36 ®) | 5 g |
| - Pigments | 10 g |

After mixing the fatty substances together under hot conditions, at a temperature below the evaporation point of the volatile fluorinated oil, the volatile oil and the pigments are introduced with stirring and the molten mixture is then poured into lipstick moulds.

After cooling and demoulding, lipsticks which have a good texture, which are easy to apply and which have a very short drying time are obtained. It is moreover observed that after drying, the lipstick does not give rise to any transfer phenomenon according to the conventional tests used for this type of determination.

In this example, the methoxynonafluorobutane can advantageously be replaced with an equivalent amount of tetradecafluorohexane or perfluorodimethylcyclohexane.

Example 2

Foundation

| | | |
|---|---|---|
| - Perfluoromethylcyclopentane (Flutec PC1 ®) | | 20 g |
| - Alkyldimethicone copolyol (Abil WE 09 ®) | | 5 g |
| - Cyclomethicone | | 10 g |
| - Pigments | | 7 g |
| - Water | qs | 100 g |

This foundation is obtained in the form of a water-in-oil (W/O) emulsion by mixing together the fatty phase and the aqueous phase with stirring. A foundation of good consistency which is easy to apply is thus obtained. It is particularly resistant to rubbing.

In this example, the perfluoromethylcyclopentane can advantageously be replaced with an equivalent amount of ethoxynonafluorobutane or 4-trifluoromethyloctafluoromorpholine.

What is claimed is:

1. A process for making transfer resistant make-up or sun-screen cosmetic composition containing particles of a substance selected from the group consisting of a pigment, filler and mixtures thereof, which consists of introducing into the said composition, a sufficient amount, as an anti-transfer agent, of a least one volatile solvent having a vapour pressure of more than 20 mbars (2000 Pa) at 25° C. said volatile solvent is a fluoroalkyl or heterofluoroalkyl compound corresponding to the following formula:

$$CH_3-(CH_2)_n-[Z]_t-X-CF_3 \qquad (II)$$

wherein

X is a linear or branched divalent perfluoroalkyl radical containing from 2 to 5 carbon atoms, and Z represents O, S or NR, R being hydrogen, a radical —$(CH_2)_n$—$CH_3$ or —$(CF_2)_m$—$CF_3$, m being 2, 3, 4 or 5, n is 0, 1, 2 or 3 and t is 0 or 1.

2. The process according to claim 1 wherein the heterofluoroalkyl compound is selected from the group consisting of methoxynonafluorobutane and ethoxynonofluorobutane.

3. The process according to claim 1 wherein said volatile solvent is present in the composition in a proportion of between 2% and 98% by weight relative to the total weight of the composition.

4. The process according to claim 1 wherein the proportion of particles in the composition is between 0.1% and 15% by weight relative to the total weight of the composition.

5. The process according to claim 1 wherein the anhydrous cosmetic composition is in the form of a mascara, eyeliner, lipstick, eyeshadow and blusher.

* * * * *